United States Patent
Frishman et al.

(10) Patent No.: US 12,044,757 B2
(45) Date of Patent: Jul. 23, 2024

(54) CLUTCHING MECHANISM FOR TELEOPERATED IN-BORE MRI GUIDED BIOPSIES

(71) Applicant: The Board of Trustees of the Leland Stanford Junior University, Stanford, CA (US)

(72) Inventors: Samuel Frishman, Stanford, CA (US); Mark R. Cutkosky, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 178 days.

(21) Appl. No.: 17/770,012

(22) PCT Filed: Nov. 12, 2020

(86) PCT No.: PCT/US2020/060138
§ 371 (c)(1),
(2) Date: Apr. 18, 2022

(87) PCT Pub. No.: WO2021/097028
PCT Pub. Date: May 20, 2021

(65) Prior Publication Data
US 2022/0390534 A1    Dec. 8, 2022

Related U.S. Application Data

(60) Provisional application No. 62/935,972, filed on Nov. 15, 2019.

(51) Int. Cl.
*A61B 10/02* (2006.01)
*A61B 17/34* (2006.01)
(Continued)

(52) U.S. Cl.
CPC ........ *G01R 33/287* (2013.01); *A61B 10/0233* (2013.01); *A61B 17/3403* (2013.01);
(Continued)

(58) Field of Classification Search
CPC ............ A61B 10/0233; A61B 17/3403; A61B 2010/0208; A61B 2017/00544; A61B 2017/00973
See application file for complete search history.

(56) References Cited

U.S. PATENT DOCUMENTS 7,854,706 B2   12/2010   Hibner
8,002,713 B2   8/2011    Heske
(Continued)

FOREIGN PATENT DOCUMENTS

WO    WO2018156522    8/2018

OTHER PUBLICATIONS

Bassett et al. Design of a mechanical clutch-based needle-insertion device.Proc Natl Acad Sci U S A. Apr. 7, 2009;106(14):5540-5. doi: 10.1073/pnas.0808274106. Epub Mar. 23, 2009. PMID: 19307560; PMCID: PMC2667015.
(Continued)

*Primary Examiner* — Rochelle D Turchen
(74) *Attorney, Agent, or Firm* — LUMEN PATENT FIRM

(57) ABSTRACT

Limited physical access to target organs of patients inside an MRI scanner is a major obstruction to real-time MRI-guided interventions. Traditional teleoperation technologies are incompatible with the MRI environment and although several solutions have been explored, a versatile system that provides high-fidelity haptic feedback and access deep inside the bore remains a challenge. A passive and nearly frictionless MRI-compatible hydraulic teleoperator is provided designed for in-bore biopsies. A needle driver translates a needle in insertion and retraction directions via a
(Continued)

clutch mechanism. A needle holder grips the needle via a retraction lock when the clutch mechanism of the needle driver releases the needle to hold a position of the needle during reposition of the needle driver.

10 Claims, 4 Drawing Sheets

(51) Int. Cl.
*G01R 33/28* (2006.01)
*A61B 17/00* (2006.01)

(52) U.S. Cl.
CPC .............. *A61B 2010/0208* (2013.01); *A61B 2017/00544* (2013.01); *A61B 2017/00973* (2013.01)

(56) References Cited

U.S. PATENT DOCUMENTS

| | | | |
|---|---|---|---|
| 8,057,402 B2 | 11/2011 | Hibner | |
| 8,672,860 B2 | 3/2014 | Moore | |
| 2002/0111634 A1* | 8/2002 | Stoianovici | A61B 90/50 |
| | | | 606/129 |
| 2004/0111183 A1 | 6/2004 | Sutherland | |
| 2021/0007817 A1* | 1/2021 | Dong | A61B 34/37 |

OTHER PUBLICATIONS

Bassett et al. Design of a mechanical clutch-based needle-insertion device. PNAS Apr. 7, 2009 106 (14) 5540-5545; https://doi.org/10.1073/pnas.0808274106.
O'Cearbhaill First published: Oct. 9, 2019 https://doi.org/10.1002/mds3.10049.

* cited by examiner

CLUTCHING MECHANISM FOR TELEOPERATED IN-BORE MRI GUIDED BIOPSIES

FIELD OF THE INVENTION

The invention relates to needle biopsy devices, methods and systems.

BACKGROUND OF THE INVENTION

Magnetic Resonance Imaging (MRI) offers physicians a safe diagnostic and therapeutic imaging modality to detect soft tissue abnormalities (e.g. tumors or inflammation). Innovations in real-time imaging technologies and MRI equipment have permitted the application of MRI guidance to a growing variety of clinical needs. MRI has potential to provide physicians with live, dynamic views of a target organ during procedures, in addition to preoperative scans. In practice, however, physicians are largely unable to perform percutaneous procedures with live scans due to dimensional constraints imposed by the bore geometry as well as MRI compatibility requirements.

MRI-guided biopsies (e.g. of the liver) are a particularly compelling example of this clinical challenge. Ideally, a physician would have the ability to remotely manipulate a biopsy needle while a patient is being imaged inside the MRI bore. In this vision, interaction forces between the needle and tissue are relayed back to the physician so that they feel as though their fingers are inside the scanner on the needle. This scenario requires equipment to be MRI compatible (i.e. producing negligible imaging artifact or distortion) which severely limits the choices of materials and technologies used for MR-guided interventions. The present invention addresses this need.

SUMMARY OF THE INVENTION

It is often desirable to perform in-bore biopsies while a patient is within an MRI system. A major challenge for in-bore biopsies is the compact space available between the patient and bore wall. Even for patients with an average BMI, there is approximately only a 20 cm gap between the patient's skin and the inner wall of the bore. The biopsy needle itself consumes a significant portion of this gap leaving little room for a device.

To address the space constraint, but still reach the necessary workspace, the inventors have created a custom MM compatible needle clutch that allows for grip and release of the needle. Using the clutch, the needle is inserted through multiple short strokes. This is similar to how a physician would drive a needle if holding it directly in hand; gripping it close to the tip, inserting partway, re-gripping further up, and then inserting deeper. The clutch allows a device to fit alongside the needle without adding additional length. The clutch enables in-bore needle biopsies which has the potential to greatly reduce procedure durations.

Preferably, the clutch supports the needle at all times, so there is never a time when the needle is supported only by tissue. Preferably a reservoir and a multiport system is used for the hydraulic lines, as opposed to only having a single port for filling the hydraulic lines of the system. Preferably a multi-axis mounting arm is used to support the needle clutch.

In one embodiment the invention is a mechanism or device for teleoperating in-bore image guided biopsies. The device includes a needle driver to translate a needle in the insertion and retraction directions. The needle driver affixes the needle along the outer surface of the needle via a clutch mechanism. The needle driver is teleoperated by a needle driver control mechanism. The device further includes a needle holder to grip the needle via a retraction lock when the clutch mechanism of the needle driver releases the needle to hold a position of the needle during reposition of the needle driver. The needle holder is teleoperated by a needle holder control mechanism.

In another embodiment, the invention is a system for teleoperating in-bore image guided biopsies. The system includes an imaging system with an in-bore area suited for imaging a patient. A needle biopsy device located within the in-bore area of an imaging system suited for taking a biopsy from the patient is further part of the system. The needle biopsy device for the system has a needle driver and a needle holder as defined earlier. Further part of the system is a needle driver to control mechanism is located outside the in-bore area of the imaging system. The needle driver control mechanism controls the needle driver within the in-bore area of an imaging system. Still further part of the system is a needle holder control mechanism is located outside the in-bore area of the imaging system. The needle holder control mechanism controls the needle holder within the in-bore area of an imaging system.

In one aspect, the needle driver control mechanism could be a hydrostatic transmission mechanism. In another aspect, the needle holder control mechanism could be a mechanical switch or pedal. In yet another aspect, the clutch mechanism could have a sleeve actuated with pneumatics. In still another aspect, the retraction lock could be actuated with pneumatics.

Some of the key advantages of the embodiments of the invention are:
  Providing the ability to remotely grip and release a biopsy needle at arbitrary positions along the needle's length;
  Providing the ability to remotely insert, retract, or manipulate a biopsy needle through multiple strokes inside an Mill bore with direct control of the needle;
  Having a needle driver and holder that can begin shorter than the length of the needle in the initial configuration;
  Enabling a remote operator to feel forces occurring at the needle; and/or
  Having a needle that is at all times supported by either the needle holder or the needle driver.

DETAILED DESCRIPTION

The exemplary teaching of the invention focuses on MM-guided liver biopsy. However, applications of embodiments of the invention are not limited to liver biopsies and are widely applicable to any type of biopsy. The liver is one of the most common organs to biopsy with the rate of liver cancer increasing. Available contrasts allow for clear and prolonged visualization of the liver under MM. Physicians have access to high contrast images of hepatic tissue for over 30 min with MM as compared to 30 s with CT. Despite these factors, few MM-guided solutions exist due to constraints that arise from the limited space between the patient and bore wall.

Figure 1:
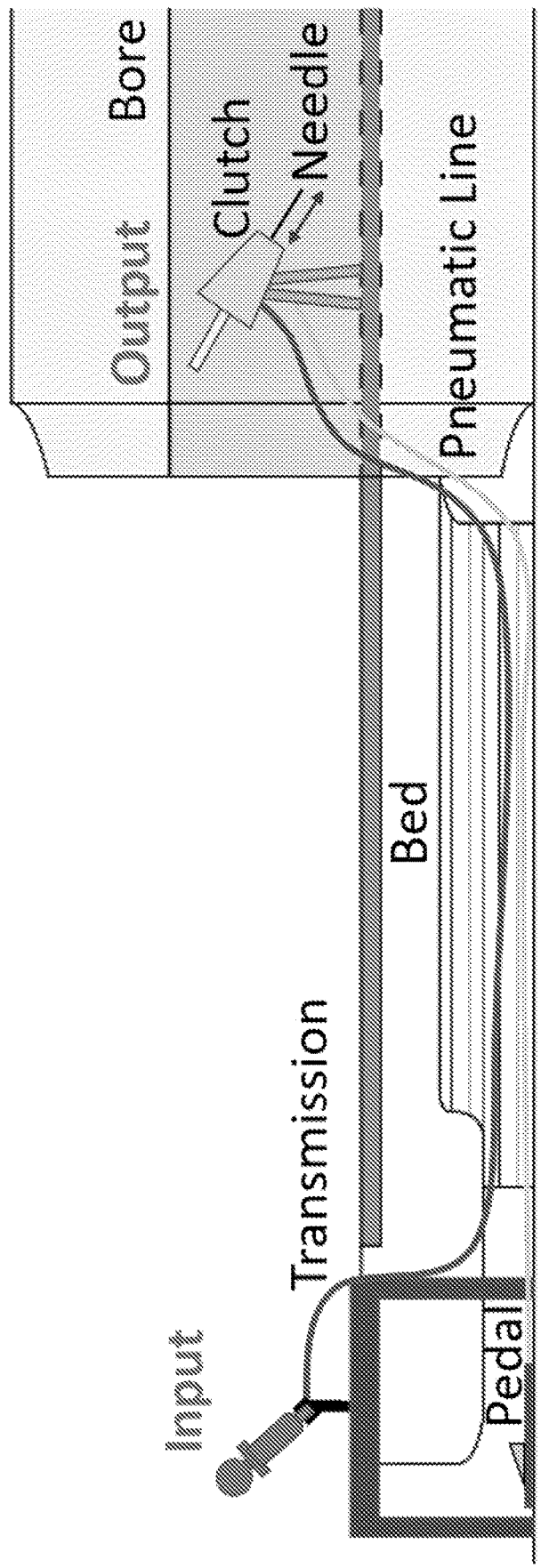
FIG. 1 shows according to an exemplary embodiment of the invention a hydrostatic teleoperation system capable of transmitting forces and motions between a physician standing outside the Mill bore and a biopsy needle within the Mill bore. A pneumatic clutch allows the physician to insert the needle with multiple short strokes. Live imaging guides the procedure, eliminating the need to move a patient in and out of the bore.

Herein a bidirectional teleoperation system is provided that accurately transmits forces and motions, enabling remote access to a patient's surgical site within the machine (FIG. 1). The teleoperator uses a hydrostatic transmission with precision-ground glass pistons and cylinders for high stiffness and nearly frictionless motion. As part of this system, an MM-compatible clutch is provided that can grip and release a biopsy needle. This allows the operator to remotely insert the biopsy needle through multiple strokes in the tight space between the patient and bore wall.

Current Standard of Care

The current standard of care for biopsies varies depending on the organ and location of suspicious targets. A common method for liver biopsies is described as the stepwise technique where a biopsy needle is iteratively positioned between imaging scans. The patient is pulled in and out of the MM bore and the needle is inserted a portion of the way each time until the tar-get tissue is reached.

This results in prolonged procedural times and preventable errors in needle placement. To improve accuracy, the use of an external optical system and instrument trackers was explored that provide updated needle visualization overlaid on an initial scan. For other organs such as the prostate, a similar paradigm is often used. Specifically, in MRI-TRUS fusion biopsy, an initial MM scan is fused with live ultra-sound. These methods seek to benefit from the superior imaging quality of MRI while providing live visualization.

Further devices have been developed with MM-compatible actuators (e.g. piezoelectric motors, pneumatic motors, electroactive polymers, or hydraulics). The location of the prostate allows these devices to be placed near the patient along the axis of the bore where there is substantial space. However, to access the liver (as well as other organs such as the breast) the device must be significantly more compact to fit between the patient and bore wall. In one approach, for both MRI and CT, one could place a significant portion of the actuation system outside the scanner and utilize a robotic arm to reach inside the bore.

Device Design

In this invention, a clutching device is provided to enable insertion of a long, stiff needle through multiple short strokes and, as a passive system, maintains the safety of manual insertion.

Figure 2:
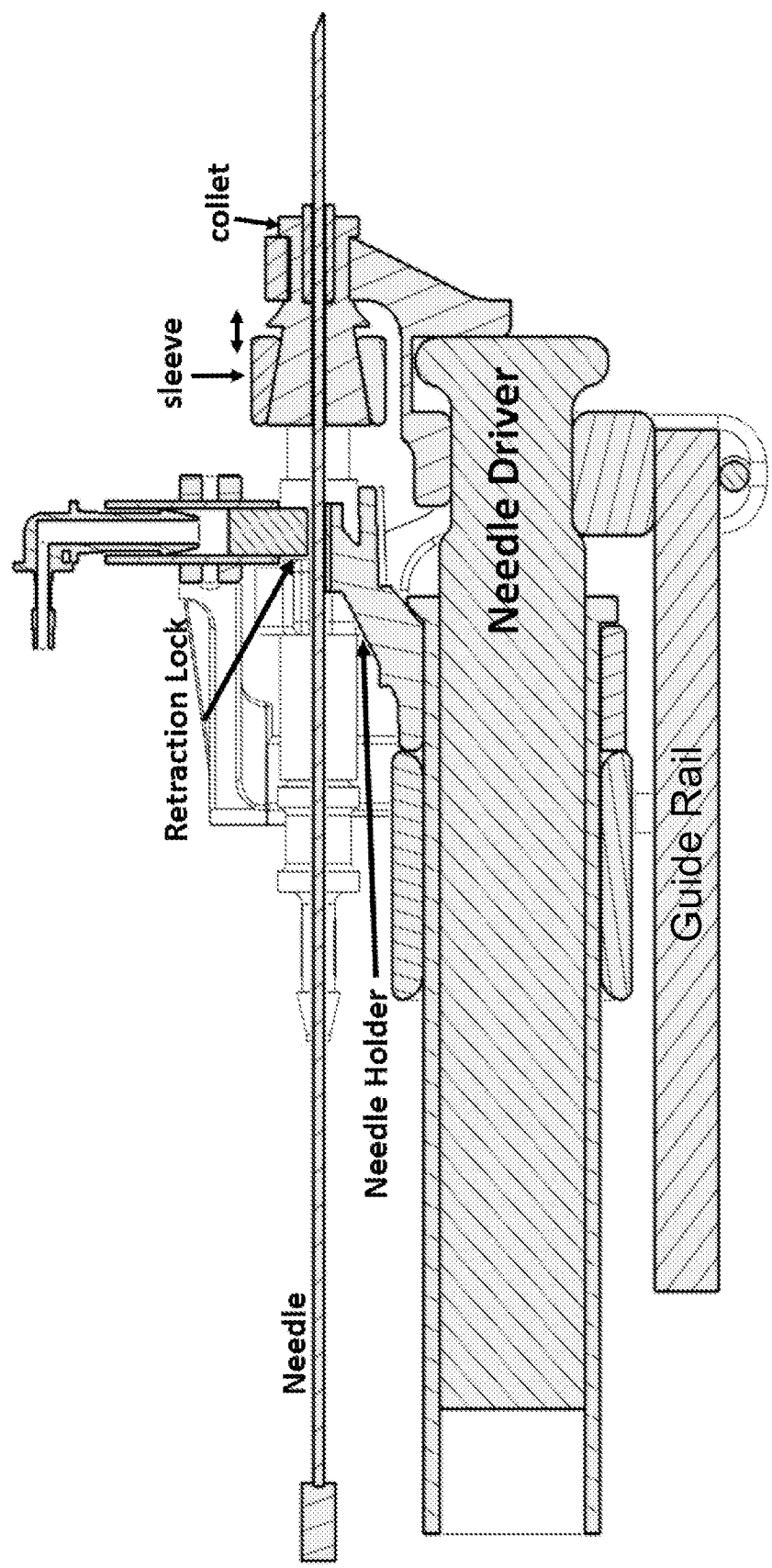
FIG. 2 shows according to an exemplary embodiment of the invention a cross section of the clutch design. A pneumatically actuated sleeve compresses the collet around the needle. A second piston locks the needle position when the collet releases. After an input stroke, the clutch is released and the hydraulic piston is retracted to re-grip the needle at a higher position. In its initial configuration, the device is shorter than the needle, enabling it to fit inside the bore. The needle driver is the component that translates the needle in the insertion and retraction directions (also referred to as hydraulic piston). The needle driver affixes (grips) the needle along its outer surface via the collet clutch mechanism. The needle holder grips the needle via the retraction lock when the collet mechanism of the needle driver releases the needle in order to hold the needle's position during reposition of the needle driver.

MRI compatibility requirements limit the choice of materials and technologies used for MRI-guided interventions. Ferrous components of any kind are incompatible, and even non-ferrous materials can cause image distortions. As noted above, the MRI bore's dimensions constrain the size and motion range available for an interventional device. To address these issues, an MRI-compatible teleoperator was developed that includes a multi-axis mounting arm for setting the initial needle alignment (FIG. 1). The device uses a hydrostatic transmission to enable access inside the MRI bore and a clutching mechanism to incrementally insert a biopsy needle. Hydraulic transmissions are a compelling choice for teleoperation as they can be designed to be MRI-compatible and have the ability to route in compact spaces. In standard 60-70 cm diameter scanners there is only about a 20 cm gap between the patient's skin and the inner wall of the bore (assuming an average body mass index). Biopsy needles are up to 15 cm long and consume a significant portion of this gap, leaving little room for a device. To address the space constraints and still reach the necessary insertion depths, a key component of the design is a custom MRI-compatible needle clutch that grips and releases the needle (FIG. 2). Using the clutch, the needle is inserted through multiple short strokes. This is similar to how a physician would drive a needle if holding it directly in hand; gripping it close to the tip, inserting part way, re-gripping further up, and inserting deeper. The transmission and clutch are described below.

Transmission

Haptic transparency of a transmission (how well forces and vibrations propagate between the input and output) depends on its stiffness and friction. With suitable tubing, hydraulic systems are inherently stiff. However, traditional hydraulic seals introduce stick-slip friction, which is undesirable for haptic applications. Users tolerate and adapt to modest amounts of added inertia, viscous friction, and hysteresis; however, the severe nonlinearities of stick-slip friction and backlash are harder to accommodate.

At each end of the transmission, custom pistons and cylinders are used adapted from ground glass syringes employed in the Loss of Resistance technique for locating the epidural space in the spine. B. Braun 10 ml glass syringes were modified by dry polishing the plunger (piston) and barrel (cylinder) and cutting away the end of the barrel to eliminate any reduction in diameter. Pipe constrictions are undesirable given that resulting friction losses grow with the ratio of diameters to the fourth power for Re<2500. 10 ml syringes were selected as they offer sufficient insertion depth (up to 5 cm) per clutch stroke and maintain a small form factor. Larger and smaller pistons can be designed for other applications.

If used with saline, as in epidural procedures, the pistons are prone to occasional binding against the cylinders. Instead, a silicone oil was selected as the working fluid. The 5 cSt oil is human-safe and represents the lowest viscosity the inventors have found that does not evaporate at room temperature and pressure.

In one example, the transmission uses reinforced tubing ($d_{tube}$=9.5 mm inner diameter, McMaster #5645K25). The tubing was sized to be similar to the piston diameter ($d_{cyl}$=15 mm) to reduce flow restrictions while maintaining a minimum bend radius of r~10 cm. Larger tubing will reduce viscous losses but increase inertia and minimum bend radius. Reinforced tubing improves transparency by reducing the compliance associated with tube expansion under pressure.

Two exemplary systems were constructed, one for use in the MRI facilities and a shorter version for laboratory experiments (3.5 m and 1.5 m respectively). The 3.5 m version enables the input to be located at the end of the MM scanner's bed while the output is inside the MRI bore at the imaging center (FIG. 1). This arrangement keeps the input outside the 5 Gauss limit where it is safe to have electrical components, such as computer monitors to display MRI scans.

Clutch

Insertion of a biopsy needle in a single stroke is impractical. Accordingly, a pneumatically actuated clutch was created that grips and releases the needle (FIGS. 1-2) to insert with multiple strokes.

In an exemplary design, the clutch utilizes a collet mechanism (FIGS. 2-3) of 3D-printed plastic (Engineering Resins Grey Pro and Tough). The collet is segmented into three leaflets with internal grooves on the surfaces that contact the needle to provide an exit path for fluid. The collet is 2 cm long, consuming less than 15% of a 15 cm biopsy needle. The collet provides a maximum axial grip force of 25 N, well above the expected forces for a liver biopsy. It is possible to adjust the maximum gripping force by changing the number of elastic bands (visible in FIG. 3).

Figure 3:
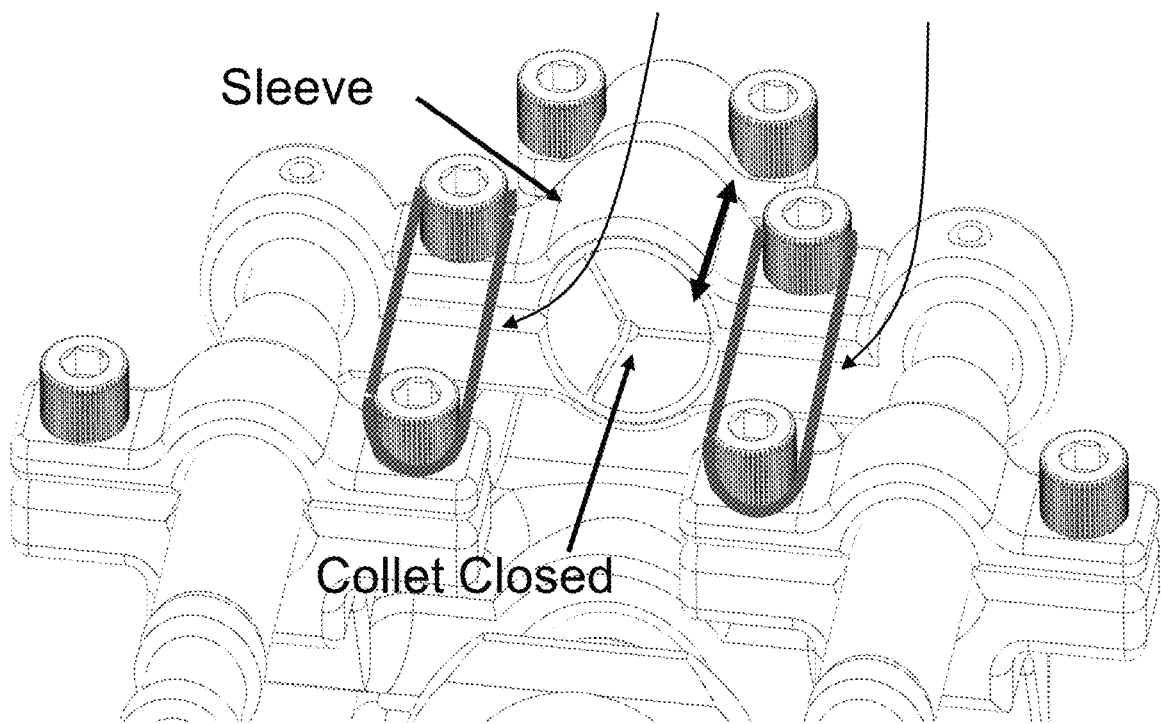
FIG. 3 shows according to an exemplary embodiment of the invention the clutch utilizing a collet mechanism.
Figure 3:
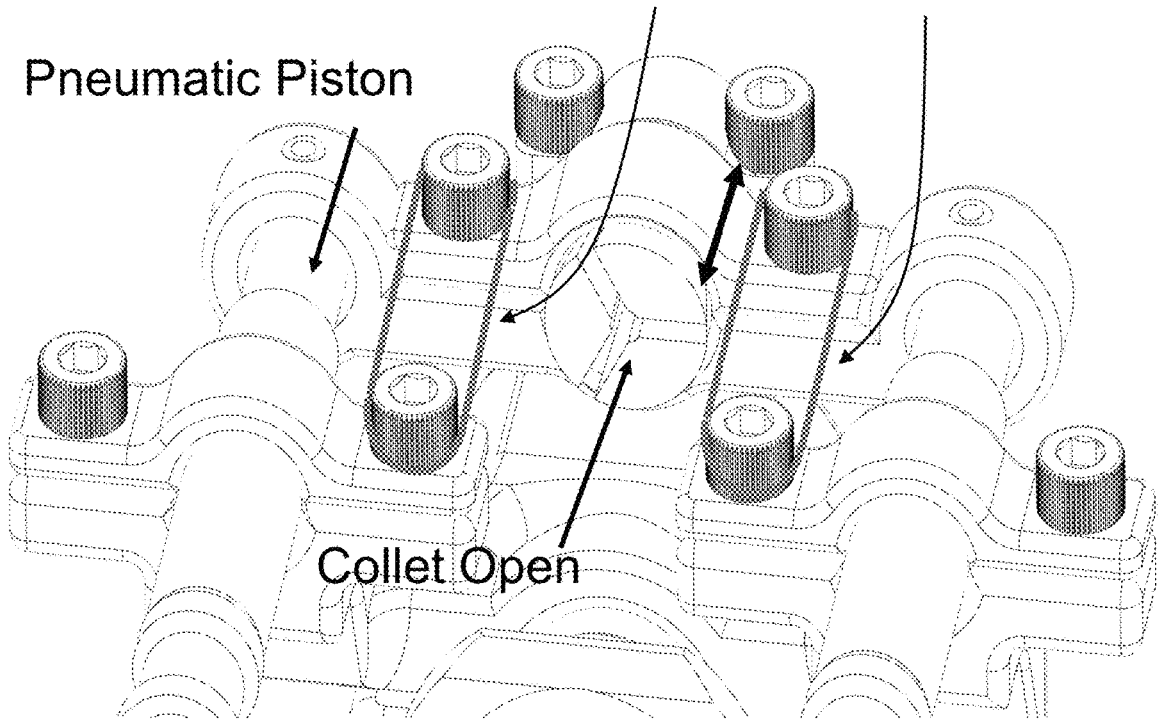

In the closed state, elastic bands slide a sleeve over the collet, forcing the leaflets to close around the needle and form a tight grip (FIG. 3). To open the collet, the operator steps on a foot pedal that actuates pneumatic pistons to slide the sleeve off the collet, which expands elastically, releasing the needle. Once the needle is released, the operator can retract and re-grip the needle higher up. When the collet is open, a retraction lock is activated, ensuring that the needle remains fixed during retraction of the piston.

Figure 4:
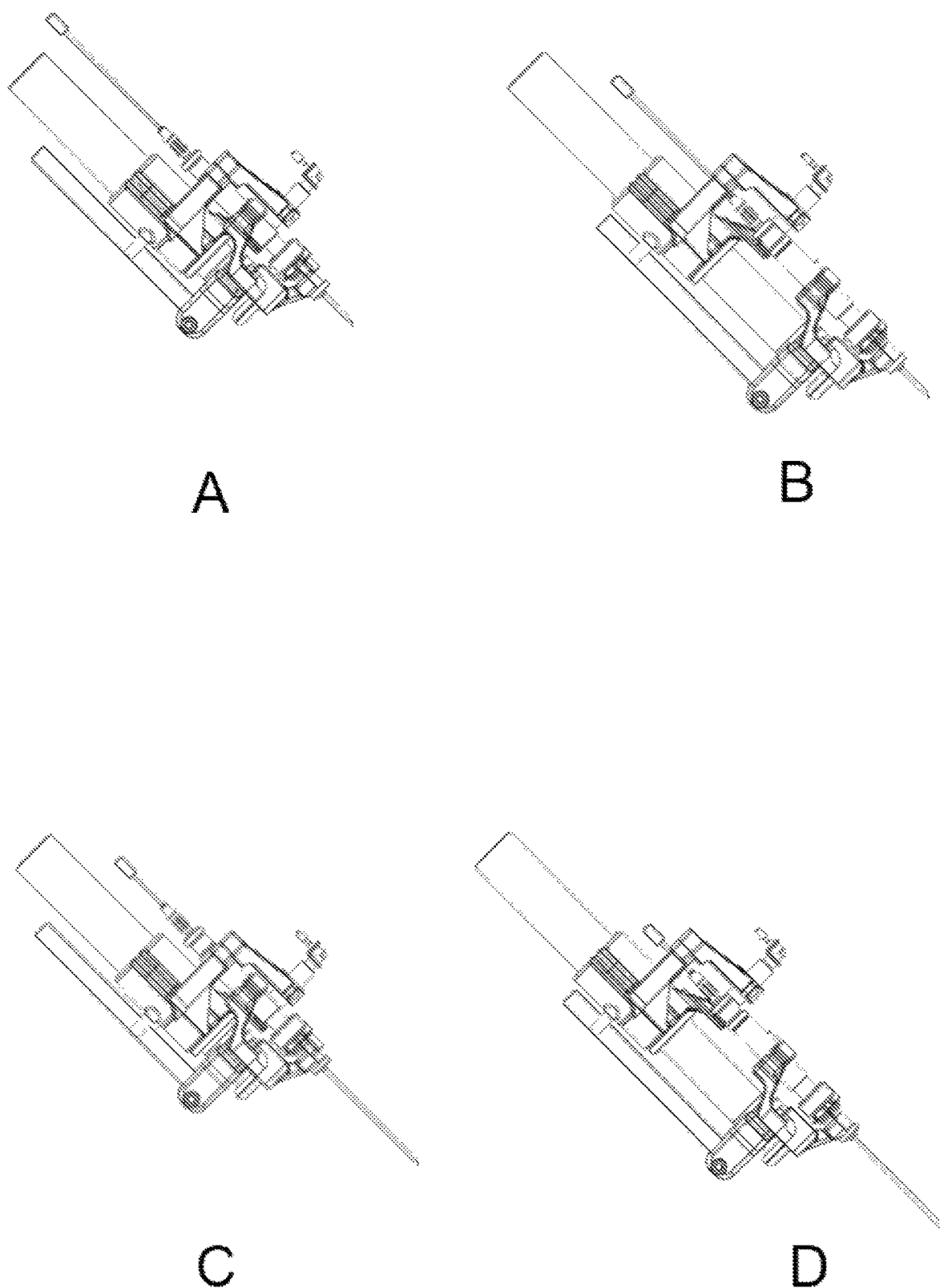
FIG. 4 shows according to an exemplary embodiment of the invention the use of the progression of the system.

FIG. 4 shows an example use of the progression of the system. The needle begins affixed to the needle driver via the closed collet and the retraction lock is not engaged (A). The operator inserts the needle at some desired distance (B). Next, the operator releases (opens) the collet clutch (e.g. by stepping on a foot pedal) and the retraction lock of the needle holder is automatically (and near simultaneously) activated. The operator retracts the needle driver, which is now free to translate with respect to the fixed needle, and re-grips the needle at a desired location by reengaging (closing) the collet (e.g. by releasing a foot pedal) (C). When the collect is reengaged (closed), the retraction lock automatically releases the needle, disengaging the needle from the needle holder and allowing the operator to again translate the needle. The operator translates the needle some desired distance (D). These steps may be repeated an arbitrary number of times to both insert and retract the needle. In this embodiment engagement/disengagement of the clutch and retraction lock are achieved via pneumatic pressure. The default state of the collet clutch is closed (needle griped by and fixed to the needle driver) and the default state of the retraction lock is open (needle not fixed to the needle holder). When an operator steps on the foot pedal, a valve is opened and pneumatic pressure is used to open the collet (release the needle from the needle driver) and activate the retraction lock (grip the needle to the needle holder). These occur nearly simultaneously as they are connected to the same pressure line. A key aspect of the device is that in its initial state (state A in FIG. 4), the device begins shorter than the length of the needle (seen in cross section view of FIG. 2). This ensures that the device fits in the space between the patient and Mill bore wall if the needle can fit.

SUMMARY

A teleoperator that enables in-bore MM-guided biopsies with haptic transparency is herein described. The teleoperator includes a stiff, low-friction hydrostatic transmission and a pneumatic clutching mechanism for incremental needle insertion. System characterization and experiments with users demonstrated the system performance. Near unity force tracking is observed at realistic manipulation speeds. Operators using the device can insert a biopsy needle with the same accuracy as if holding the needle directly in hand. The system is constructed of non-conductive materials and has negligible impact on imaging SNR. The inherent safety and low cost of a passive system can facilitate its adoption, as a step towards clinical use of in-bore MM guided interventions.

What is claimed is:

1. A device for teleoperating in-bore image guided biopsies, comprising:
   (a) a needle driver to translate a needle in insertion and retraction directions where the directions are defined in a longitudinal direction of the needle, wherein the needle driver affixes the needle along the outer surface of the needle via a clutch mechanism, wherein the needle driver is teleoperated by a needle driver control mechanism; and
   (b) a needle holder to grip the needle via a retraction lock when the clutch mechanism of the needle driver releases the needle to hold a position of the needle during reposition of the needle driver, wherein the needle holder is teleoperated by a needle holder control mechanism.

2. The device as set forth in claim 1, wherein the needle driver control mechanism is a hydrostatic transmission.

3. The device as set forth in claim 1, wherein the needle holder control mechanism is a mechanical switch or pedal.

4. The device as set forth in claim 1, wherein the clutch mechanism comprises a sleeve actuated with pneumatics.

5. The device as set forth in claim 1, wherein the retraction lock is actuated with pneumatics.

6. A system for teleoperating in-bore image guided biopsies, comprising:
   (a) an imaging system with an in-bore area suited for imaging a patient;
   (b) a needle biopsy device located within the in-bore area of an imaging system suited for taking a biopsy from the patient, wherein the needle biopsy device comprises:
      (i) a needle driver to translate a needle in insertion and retraction directions where the directions are defined in a longitudinal direction of the needle, wherein the needle driver affixes the needle along the outer surface of the needle via a clutch mechanism; and
      (ii) a needle holder to grip the needle via a retraction lock when the clutch mechanism of the needle driver releases the needle to hold a position of the needle during reposition of the needle driver;
   (c) a needle driver control mechanism located outside the in-bore area of the imaging system, wherein the needle driver control mechanism controls the needle driver within the in-bore area of an imaging system; and
   (d) a needle holder control mechanism located outside the in-bore area of the imaging system, wherein the needle holder control mechanism controls the needle holder within the in-bore area of an imaging system.

7. The system as set forth in claim 6, wherein the needle driver control mechanism is a hydrostatic transmission.

8. The system as set forth in claim 6, wherein the needle holder control mechanism is a mechanical switch or pedal.

9. The system as set forth in claim 6, wherein the clutch mechanism comprises a sleeve actuated with pneumatics.

10. The system as set forth in claim 6, wherein the retraction lock is actuated with pneumatics.

\* \* \* \* \*

UNITED STATES PATENT AND TRADEMARK OFFICE
CERTIFICATE OF CORRECTION

| | | |
|---|---|---|
| PATENT NO. | : 12,044,757 B2 | Page 1 of 1 |
| APPLICATION NO. | : 17/770012 | |
| DATED | : July 23, 2024 | |
| INVENTOR(S) | : Samuel Frishman | |

It is certified that error appears in the above-identified patent and that said Letters Patent is hereby corrected as shown below:

In the Specification

Insert:
--Statement of Government Sponsored Support
This invention was made with Government support under contract 1615891 awarded by the National Science Foundation. The Government has certain rights in the invention.--

Signed and Sealed this
Seventeenth Day of September, 2024

Katherine Kelly Vidal
*Director of the United States Patent and Trademark Office*